(12) United States Patent
Irudayaraj et al.

(10) Patent No.: US 10,611,749 B2
(45) Date of Patent: Apr. 7, 2020

(54) PROCESS FOR PREPARATION OF ROTIGOTINE AND INTERMEDIATES THEREOF

(71) Applicant: Solara Active Pharma Sciences Limited, Chennai (IN)

(72) Inventors: Victor Paul Raj Irudayaraj, Chennai (IN); Senthilkumar Subramani, Krishnagiri (IN); Vedhachalam Govindaraj, Chennai (IN); Jeyakanthan Jayavelu, Thiruvannamalai (IN); Boopathy Jayaraman, Thanjavur (IN); Uttam Kumar Ray, Chennai (IN); Tangirala Vittal, Chennai (IN)

(73) Assignee: Solara Active Pharma Sciences Limited, Navi Mumbai (IN)

( * ) Notice: Subject to any disclaimer, the term of this patent is extended or adjusted under 35 U.S.C. 154(b) by 0 days.

(21) Appl. No.: 16/275,634

(22) Filed: Feb. 14, 2019

(65) Prior Publication Data

US 2019/0248758 A1    Aug. 15, 2019

(30) Foreign Application Priority Data

Feb. 15, 2018    (IN) .............................. 201841005876

(51) Int. Cl.
*C07D 333/20* (2006.01)

(52) U.S. Cl.
CPC .................. *C07D 333/20* (2013.01)

(58) Field of Classification Search
CPC .................................. C07D 333/20
USPC ......................................... 549/75
See application file for complete search history.

(56) References Cited

U.S. PATENT DOCUMENTS

| | | | |
|---|---|---|---|
| 4,564,628 A | 1/1986 | Horn | |
| 4,885,308 A | 12/1989 | Horn | |
| 6,372,920 B1 | 4/2002 | Minaskanian et al. | |
| 8,519,160 B2 * | 8/2013 | Banfi ................... | C07C 213/08 549/75 |
| 8,614,337 B2 | 12/2013 | He et al. | |
| 2011/0313176 A1 | 12/2011 | Khunt et al. | |

FOREIGN PATENT DOCUMENTS

WO    2010073124 A2    7/2010

OTHER PUBLICATIONS

Cobley et al., Tetrahedron Letters, 57(2016), pp. 986-989.*

* cited by examiner

*Primary Examiner* — Niloofar Rahmani
(74) *Attorney, Agent, or Firm* — The Webb Law Firm

(57) ABSTRACT

The present invention relates to a novel process for the preparation of Rotigotine of formula (I) and intermediates thereof.

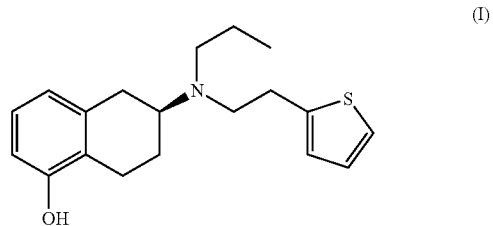

(I)

6 Claims, No Drawings

PROCESS FOR PREPARATION OF ROTIGOTINE AND INTERMEDIATES THEREOF

CROSS-REFERENCE TO RELATED APPLICATION

This application claims priority to Indian Patent Application No. 201841005876 filed Feb. 15, 2018, the disclosure of which is hereby incorporated by reference in its entirety.

FIELD OF THE INVENTION

The present invention relates to a novel process for the preparation of Rotigotine and intermediates thereof.

BACKGROUND OF THE INVENTION

Rotigotine is chemically known as (6S)-6-{propyl [2-(2-thienyl)ethyl]amino}-5,6,7,8-tetrahydro-1-naphthalenol having the formula (I) as mentioned below.

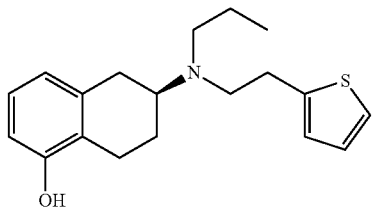

(I)

Rotigotine is marketed as Neupro in US and Europe for the treatment of Parkinson's disease. Rotigotine was first disclosed in the U.S. Pat. No. 4,564,628.

The U.S. Pat. No. 4,564,628 discloses two processes for the preparation of Rotigotine. One of the processes is depicted in Scheme-1.

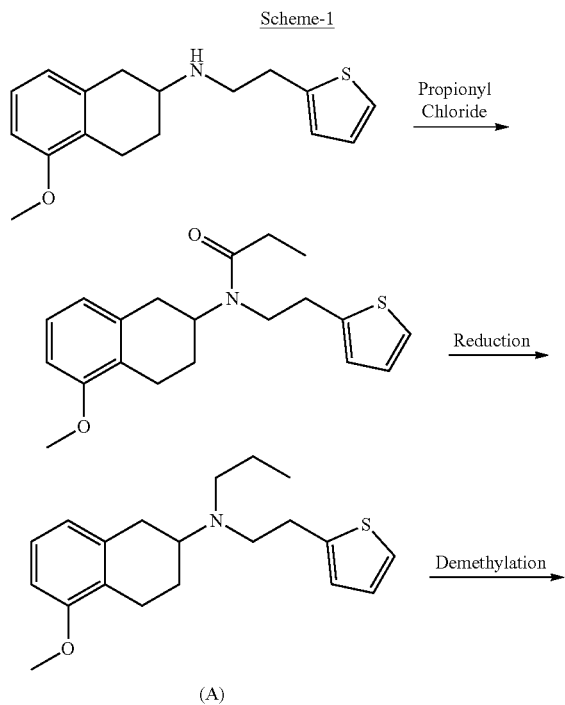

Scheme-1

(A)

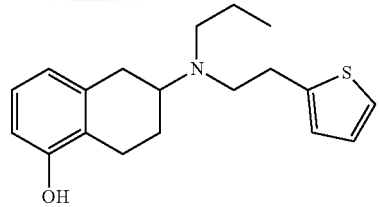

In this scheme, the compound 1,2,3,4-tetrahydro-5-methoxy-N-propyl-N-[2-(2-thienyl)ethyl]-2-naphthaleneamine (A) is prepared from the reaction of 1,2,3,4-tetrahydro-5-methoxy-N-[2-(thienyl)-ethyl]-2-naphthaleneamine with propionyl chloride to form an intermediate followed by the reduction of the formed intermediate. The compound 1,2,3,4-tetrahydro-5-methoxy-N-propyl-N-[2-(2-thienyl)ethyl]-2-naphthaleneamine (A) is then demethylated to form racemic Rotigotine.

Another process involves the preparation of the intermediate 1,2,3,4-tetrahydro-5-methoxy-N-propyl-N-[2-(2-thienyl)ethyl]-2-naphthaleneamine (A) from the reaction of 1,2,3,4-tetrahydro-5-methoxy-N-propyl-2-naphthaleneamine with 2-thienylacetic acid in presence of borane trimethylamine complex as depicted in Scheme-2. The prepared intermediate (A) in this process is then demethylated to form Rotigotine.

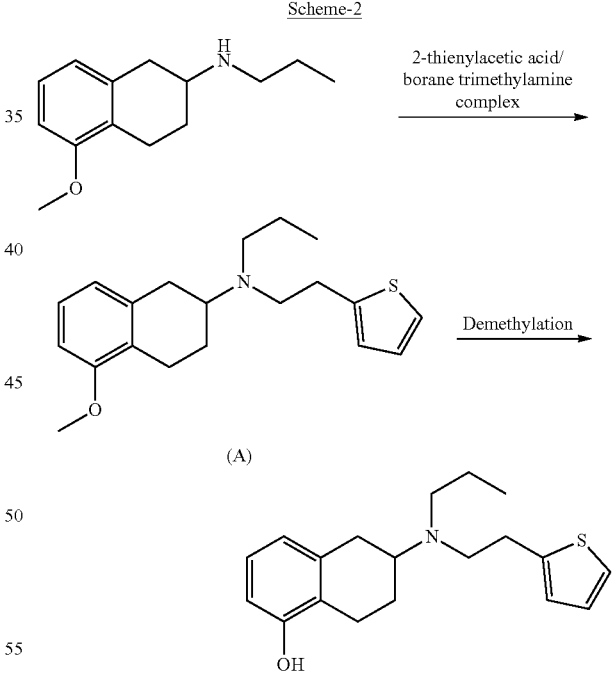

Scheme-2

(A)

The transformation of intermediate (A) into Rotigotine involves the demethylation of compound (A) in the presence of boron tribromide at low temperature in inert solvents. After the completion of this reaction, the excess boron tribromide was destroyed by addition of methanol.

The use of 48% hydrobromic acid for the demethylation of the compound (A) reported in literature, yielded N-dealkylated impurities along with Rotigotine. The structural similarity of the impurities and Rotigotine makes the purification problematic through physical methods.

The use of boron tribromide for the demethylation of the compound (A) to obtain Rotigotine reported in literature, has to be carried out at low temperatures of −30° C. to −40° C. Performing reaction at such low temperatures and cumbersome processes involving the treatment of excess of boron tribromide makes this process less preferable on commercial scale.

The use of aluminium chloride along with thiourea for the demethylation of the compound (A) to obtain Rotigotine as disclosed in the International Publication No. 2010073124 results in Rotigotine with impurities. These impurities formed at this stage are not easy to purify from Rotigotine. Further multiple stages of purification of Rotigotine from these impurities causes yield loss in the final API.

The U.S. Pat. No. 4,885,308 discloses a process for preparation of Rotigotine involving the resolution of racemic 2-(N-propylamino)-5-methoxytetralin to get desired enantiomer and then converting the desired enantiomer to Rotigotine, using the process disclosed in U.S. Pat. No. 4,564,628.

The U.S. Pat. No. 6,372,920 discloses a process for preparing Rotigotine involving the step of reacting (−)-5-hydroxy-N-n-propyl-2-aminotetralin with 2-(2-thienyl)ethanol toluene sulfonate in the presence of alkali metal carbonate or alkali metal bicarbonate.

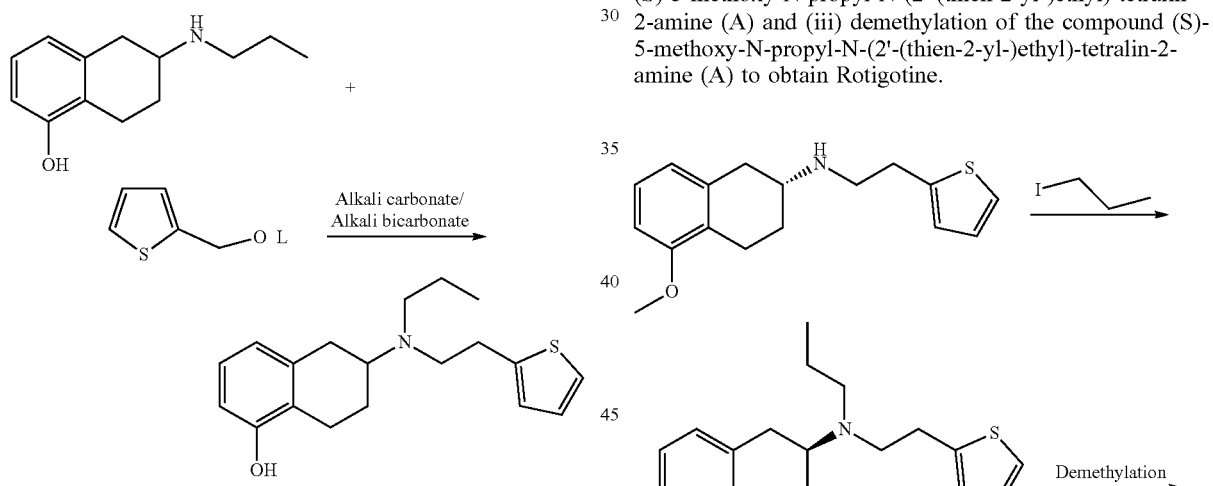

The U.S. Pat. No. 8,519,160 discloses a process for the preparation of Rotigotine involving the steps of (i) demethylation of 2-N-propyl-5-methoxy tetraline by the treatment with 48% hydrobromic acid to obtain 2-N-propyl-5-hydroxy tetraline base; and (ii) the reaction of the obtained 2-N-propyl-5-hydroxy tetraline base with 2-thienylacetic acid-sodium borohydride complex in toluene to obtain Rotigotine free base.

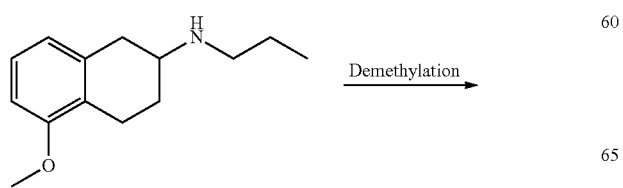

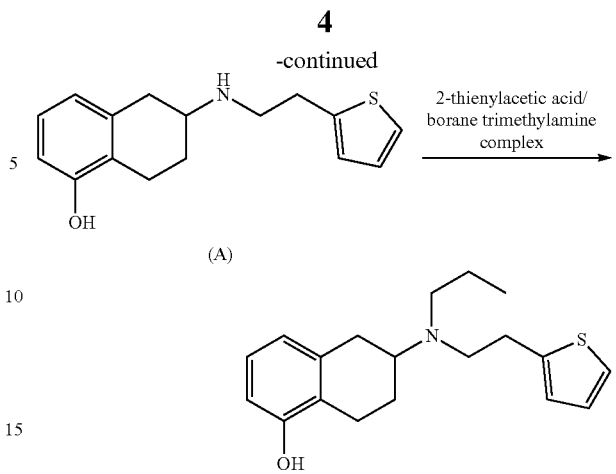

Bromo impurities formed during the demethylation of the compound 2-N-propyl-5-methoxy tetraline using 48% hydrobromic acid to obtain 2-N-propyl-5-hydroxy tetraline base are difficult to remove from the obtained 2-N-propyl-5-hydroxy tetraline base.

The U.S. Pat. No. 8,614,337 discloses a method for preparing Rotigotine which involves the steps of: (i) resolution of racemic to obtain (S)-5-methoxy-N-2'-(thien-2-yl-)ethyl-tetralin-2-amine; and (ii) reaction of the resolved enantiomer with iodopropane in presence of base to yield (S)-5-methoxy-N-propyl-N-(2'-(thien-2-yl-)ethyl)-tetralin-2-amine (A) and (iii) demethylation of the compound (S)-5-methoxy-N-propyl-N-(2'-(thien-2-yl-)ethyl)-tetralin-2-amine (A) to obtain Rotigotine.

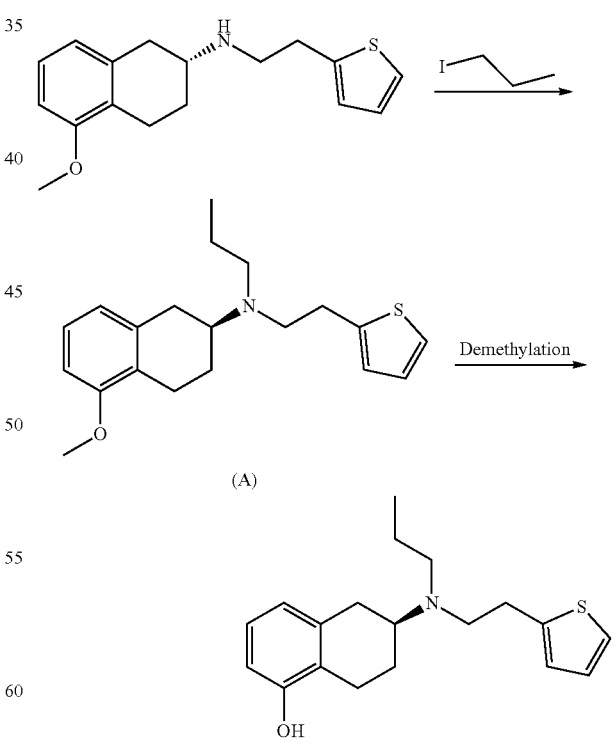

Besides the availability of different processes for the preparation Rotigotine in state of the art, there is a need for alternative process for the preparation of Rotigotine that would be economically significant than the others.

OBJECTIVE OF THE INVENTION

An object of the invention is to provide an efficient and industry feasible process for the preparation of Rotigotine.

Another object of the invention is to provide a novel process for preparation of intermediates for Rotigotine.

SUMMARY OF THE INVENTION

Accordingly, there is provided an improved process for the preparation of Rotigotine and the intermediates thereof.

One of an aspect of the present invention is to provide a process for the preparation of Rotigotine of formula (I),

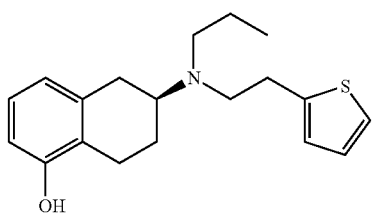
(I)

said process comprising the steps of:
(i) reacting the compound (S)-1,2,3,4-tetrahydro-5-methoxy-N-propyl-2-naphthalenamine of formula (IV) or its salt thereof

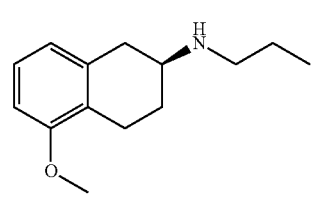
(IV)

with 2-thienylacetic acid derivative of formula (V) or its salt thereof,

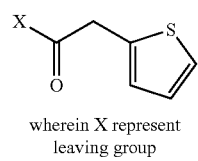
(V)

wherein X represent leaving group presence of base to obtain a compound (2S)—N-(5-methoxy-1,2,3,4-tetrahydro-naphthalen-2-yl)-N-propyl-2-thiophen-2-yl-acetamide of formula (III) or its salt thereof;

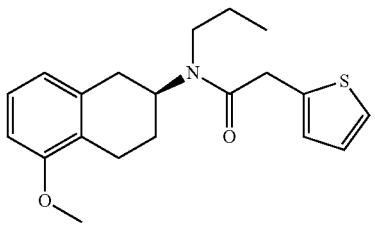
(III)

(ii) demethylating the compound (2S)—N-(5-methoxy-1,2,3,4-tetrahydro-naphthalen-2-yl)-N-propyl-2-thiophen-2-yl-acetamide of formula (III) or its salt thereof obtained in step (i) with aluminium chloride to obtain a compound (2S)—N-(5-hydroxy-1,2,3,4-tetrahydro-naphthalen-2-yl)-N-propyl-2-thiophen-2-yl-acetamide of formula (II) or its salt thereof;

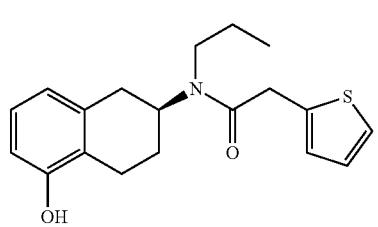
(II)

(iii) reducing the compound of formula (II) obtained in step (ii) with a suitable reducing agent in a solvent to obtain Rotigotine of formula (I) or its salt thereof;

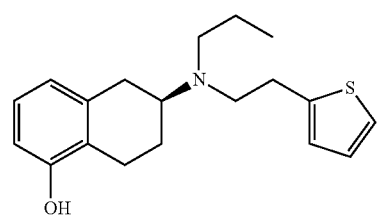
(I)

(iv) optionally liberating the Rotigotine free base from the salt obtained in step (iii) in presence of suitable base and solvent; and
(v) isolating Rotigotine as free base from the reaction mass obtained in step (iii) or step (iv).

In some embodiment of the invention, in the above described process for the preparation of Rotigotine, the said leaving group is selected from the group comprising of halogen such as chlorine, bromine or iodine; alkylsulfonyloxy such as trifluoromethylsulfonyloxy; or arylsulfonyloxy such as benzenesulfonyloxy.

In some embodiment of the invention, in the above described process for the preparation of Rotigotine, the base is selected from the group comprising of hydroxide or carbonate salt of alkali or alkaline earth metals. In some embodiment, the base is selected from the group comprising of lithium hydroxide, potassium hydroxide, sodium hydroxide, calcium hydroxide, sodium carbonate, sodium hydrogen carbonate, potassium carbonate, calcium carbonate or cesium carbonate.

In some other embodiment of the invention, in the above described process for the preparation of Rotigotine, the base is selected from the group comprising of organic bases.

Another aspect of the present invention is to provide a process for the preparation of compound (2S)—N-(5-hydroxy-1,2,3,4-tetrahydro-naphthalen-2-yl)-N-propyl-2-thiophen-2-yl-acetamide of formula (II) or its salt thereof

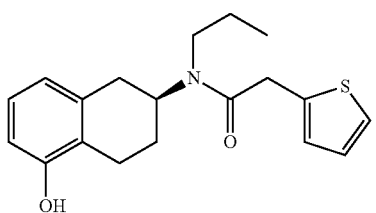

(II)

said process comprising the steps of:
(i) reacting the compound (S)-1,2,3,4-tetrahydro-5-methoxy-N-propyl-2-naphthalenamine of formula (IV) or its salt thereof

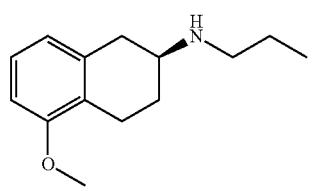

(IV)

with 2-thienylacetic acid derivative of formula (III) or its salt thereof

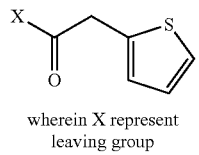

(V)

wherein X represent leaving group in presence of base to obtain a compound (2S)—N-(5-methoxy-1,2,3,4-tetrahydro-naphthalen-2-yl)-N-propyl-2-thiophen-2-yl-acetamide of formula (III) or its salt thereof; and

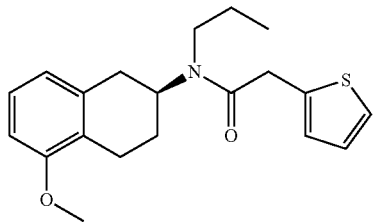

(III)

(ii) demethylating the compound (2S)—N-(5-methoxy-1,2,3,4-tetrahydro-naphthalen-2-yl)-N-propyl-2-thiophen-2-yl-acetamide of formula (III) or its salt thereof as obtained in step (i) with aluminium chloride to obtain a compound (2S)—N-(5-hydroxy-1,2,3,4-tetrahydro-naphthalen-2-yl)-N-propyl-2-thiophen-2-yl-acetamide of formula (II) or its salt thereof.

In some embodiment of the invention, in the above described process for the preparation of compound of formula (II), the said base is selected from the group comprising of hydroxides or carbonate salt of alkali or alkaline earth metals. In some embodiment, the said base is selected from the group comprising of lithium hydroxide, potassium hydroxide, sodium hydroxide, calcium hydroxide, sodium carbonate, sodium hydrogen carbonate, potassium carbonate, calcium carbonate or cesium carbonate. In some embodiment of the invention, the said base is selected from the group comprising of organic bases.

Yet another aspect of the present invention is to provide a process for the preparation of compound (2S)—N-(5-hydroxy-1,2,3,4-tetrahydro-naphthalen-2-yl)-N-propyl-2-thiophen-2-yl-acetamide of formula (II) or its salt thereof,

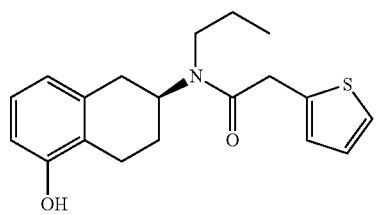

(II)

by demethylating a compound (2S)—N-(5-methoxy-1,2,3,4-tetrahydro-naphthalen-2-yl)-N-propyl-2-thiophen-2-yl-acetamide of formula (III) or its salt thereof,

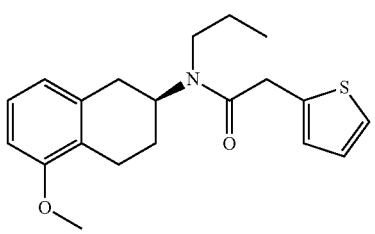

(III)

with aluminium chloride to obtain a compound (2S)—N-(5-hydroxy-1,2,3,4-tetrahydro-naphthalen-2-yl)-N-propyl-2-thiophen-2-yl-acetamide of formula (II) or its salt thereof.

In some embodiment of the invention, there is provided a process for the preparation of Rotigotine which is stable for more than 3 months at 20-40° C. and 65%-75% of relative humidity.

DESCRIPTION OF THE INVENTION

The present invention provides an improved process for the preparation of Rotigotine and the various aspects and embodiments of the present invention are described herein details.

One aspect of the present invention is to provide a process for the preparation of Rotigotine of formula (I)

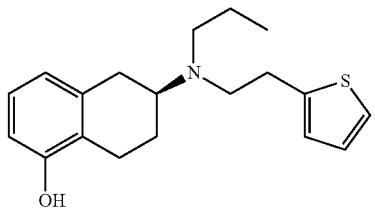

(I)

said process comprising the steps of:
(i) reacting the compound (S)-1,2,3,4-tetrahydro-5-methoxy-N-propyl-2-naphthalenamine of formula (IV) or its salt thereof

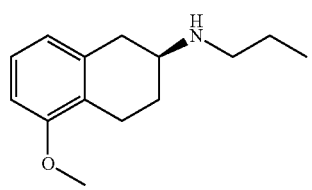

(IV)

with 2-thienylacetic acid derivative of formula (V) or its salt thereof,

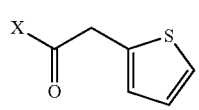

(V)

wherein X represent leaving group in presence of base to obtain a compound (2S)—N-(5-methoxy-1,2,3,4-tetrahydro-naphthalen-2-yl)-N-propyl-2-thiophen-2-yl-acetamide of formula (III) or its salt thereof;

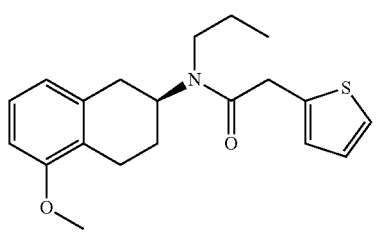

(III)

(ii) demethylating the compound (2S)—N-(5-methoxy-1,2,3,4-tetrahydro-naphthalen-2-yl)-N-propyl-2-thiophen-2-yl-acetamide of formula (III) or its salt thereof obtained in step (i) with aluminium chloride to obtain a compound (2S)—N-(5-hydroxy-1,2,3,4-tetrahydro-naphthalen-2-yl)-N-propyl-2-thiophen-2-yl-acetamide of formula (II) or its salt thereof;

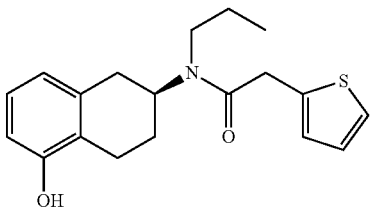

(II)

(iii) reducing the compound of formula (II) obtained in step (ii) with a suitable reducing agent in a solvent to obtain Rotigotine of formula (I) or its salt thereof;
(iv) optionally liberating the Rotigotine free base from the salt obtained in step (iii) in presence of suitable base and solvent; and
(v) isolating Rotigotine as free base from the reaction mass obtained in step (iii) or step (iv).

In some embodiment of the invention, the said "X" in compound of formula (V) as mentioned in step (i) represents a leaving group. Preferred leaving group is halogen such as chlorine, bromine and iodine; alkylsulfonyloxy such as trifluoromethylsulfonyloxy; or arylsulfonyloxy such as benzenesulfonyloxy.

In some embodiment of the invention, the base used in the step (i) of the above described process for the preparation of Rotigotine is selected from the group comprising but not limited to hydroxide or carbonate salt of alkali or alkaline earth metals or organic bases. Preferred base selected form a group comprising lithium hydroxide, potassium hydroxide, sodium hydroxide, calcium hydroxide, sodium carbonate, sodium hydrogen carbonate, potassium carbonate, calcium carbonate, cesium carbonate and the like. More preferably carbonate of sodium or potassium and most preferably sodium carbonate.

In some embodiment of the invention, the solvent employed in step (i) of the above described process for the preparation of Rotigotine is selected from the group including but not limited to class of hydrocarbons, halogenated hydrocarbons, esters, ethers, alcohols, water or mixtures thereof. Preferred toluene, xylene, hexane, heptane, cyclohexane, dichloromethane, dichloroethane, trichloromethane, ethyl acetate, methyl acetate, propyl acetate, diethyl ether, diisopropyl ether, water or the mixtures thereof, most preferably toluene.

In some embodiment of the invention, the N-acylation reaction of the step (i) of the above described process for the preparation of Rotigotine is carried under condition sufficient to allow formation of compound (2S)—N-(5-methoxy-1,2,3,4-tetrahydro-naphthalen-2-yl)-N-propyl-2-thiophen-2-yl-acetamide of formula (III) or salt thereof which include but not limited to heating or cooling, stirring the reaction mass for sufficient duration. In some embodiment of the invention, the formed compound of formula (III) or salt thereof is isolated from the reaction mass by the techniques known in the state of art, preferably involving the steps of separating the immiscible organic solvent and removing the immiscible organic solvent to obtain a residue that is purified by methods known in the state of art.

In some embodiment of the invention, demethylation of step (ii) of the process for the preparation of Rotigotine is carried out in the presence of from 0.5 to 8, advantageously from 1 to 3, mole of aluminium chloride per mole of starting material.

In some embodiment of the invention, the solvent employed in step (ii) of the process for the preparation of Rotigotine is selected from the group including but not limited to class of hydrocarbons, halogenated hydrocarbons or mixtures thereof. Preferred toluene, xylene, hexane, heptane, cyclohexane, dichloromethane, dichloroethane, trichloromethane, monochlorobenzene or the mixture thereof, most preferably toluene.

In some embodiment, the reducing agent in step (iii) of the process for the preparation of Rotigotine is selected from the group including but not limited to catalytic hydrogenation, lithium aluminium hydride ($LiAlH_4$), diisobutylaluminium hydride (DIBAL-H), diborane ($B_2H_6$), borane dimethyl sulphide (($CH_3)_2S$—$BH_3$), trimethylamine borane (($CH_3)_3N$—$BH_3$), borane-THF complex ($BH_3OC_4H_8$), and the likes. Preferably borane hydride complex derivatives, most preferably borane dimethyl sulphide ($CH_3)_2S$—$BH_3$.

In some embodiment of the invention, the solvent employed in step (iii) is selected from the group comprising toluene, xylene, tetrahydrofuran, 1,4-dioxane or the like.

The reductive reaction of amide of formula (II) is performed under condition sufficient to allow formation of Rotigotine or salt thereof.

The formed Rotigotine of formula (I) in the process according to invention is isolated from the reaction mass by the techniques known in the art, preferably involving the steps of separating the organic solvent and removing the organic solvent to obtain a residue that is purified by methods known in the state of art.

In some embodiment of the invention, the Rotigotine obtained is converted into a suitable salt for better isolation and purification of Rotigotine of formula (I). Most preferably Rotigotine of formula (I) is isolated as salt after completion of the reduction of compound of formula (II).

Preferably, the salt obtained in step (iii) is converted into a free base comprising the steps of providing a solution of salt of Rotigotine of formula (I) in biphasic solvent system in presence of base and separating the organic solvent layer containing Rotigotine free base.

In some embodiment of the invention, the biphasic solvent system in the preparation of Rotigotine free base from Rotigotine hydrochoride comprises a mixture of two immiscible solvents, of which one is water and other is a water immiscible organic solvent. The immiscible organic solvent includes but not limited to class of hydrocarbons, halogenated hydrocarbons, esters, ethers, etc. Preferred employable immiscible organic solvents comprise of group selected from toluene, xylene, hexane, heptane, cyclohexane, dichloromethane, dichloroethane, trichloromethane, ethyl acetate, methyl acetate, propyl acetate, diethyl ether, diisopropyl ether and the likes, more preferably ester and most preferably ethyl acetate.

In some embodiment, the suitable base employed in step (iv) of the process for the preparation of Rotigotine is selected from the group including but not limited to hydroxide or carbonate salt of alkali or alkaline earth metals. More preferably carbonate of sodium or potassium.

Surprisingly, the inventors of this invention found that, demethylating the (2S)—N-(5-methoxy-1,2,3,4-tetrahydro-naphthalen-2-yl)-N-propyl-2-thiophen-2-yl-acetamide of formula (II) or its salt thereof with aluminium chloride to obtain a compound (2S)—N-(5-hydroxy-1,2,3,4-tetrahydro-naphthalen-2-yl)-N-propyl-2-thiophen-2-yl-acetamide of formula (II) or its salt thereof for preparing Rotigotine is economically advantageous over the other prior art process, since the formation of impurities during this step is less and easily removable by techniques known in the art.

Another aspect of the present invention is to provide a process for the preparation of compound (2S)—N-(5-hydroxy-1,2,3,4-tetrahydro-naphthalen-2-yl)-N-propyl-2-thiophen-2-yl-acetamide of formula (II) or its salt thereof,

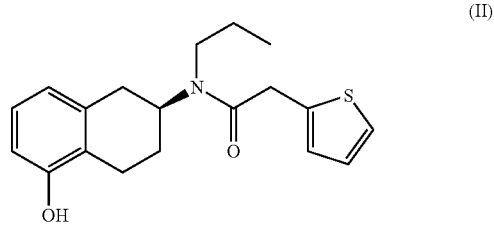 [SMILES: CCCN(C(=O)Cc1cccs1)[C@H]1CCc2c(O)cccc2C1]

(II)

said process comprising the steps of:
(i) reacting the compound (S)-1,2,3,4-tetrahydro-5-methoxy-N-propyl-2-naphthalenamine of formula (IV) or its salt thereof

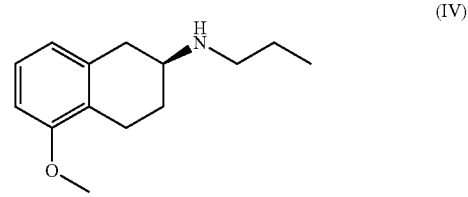 [SMILES: CCCN[C@H]1CCc2c(cccc2OC)C1]

(IV)

with 2-thienylacetic acid derivative of formula (III) or its salt thereof

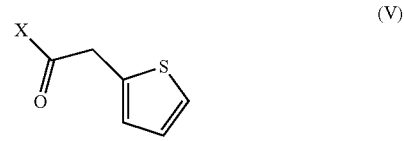

(V)

wherein X represent leaving group in presence of base to obtain a compound (2S)—N-(5-methoxy-1,2,3,4-tetrahydro-naphthalen-2-yl)-N-propyl-2-thiophen-2-yl-acetamide of formula (III) or its salt thereof; and

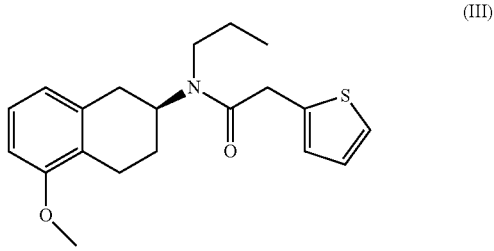 [SMILES: CCCN(C(=O)Cc1cccs1)[C@H]1CCc2c(cccc2OC)C1]

(III)

(ii) demethylating the compound (2S)—N-(5-methoxy-1,2,3,4-tetrahydro-naphthalen-2-yl)-N-propyl-2-thiophen-2-yl-acetamide of formula (III) or its salt thereof as obtained in step (i) with aluminium chloride to obtain a compound (2S)—N-(5-hydroxy-1,2,3,4-tetrahydro-naphthalen-2-yl)-N-propyl-2-thiophen-2-yl-acetamide of formula (II) or its salt thereof.

In some embodiment, the said "X" in compound of formula (III) as mentioned in step (i) of the process for the preparation of compound of formula (II) represents a leaving group. Preferred leaving group is halogen such as chlorine, bromine and iodine; alkylsulfonyloxy such as trifluoromethylsulfonyloxy; or arylsulfonyloxy such as benzenesulfonyloxy.

In some embodiment of the invention, in step (i) of the process for the preparation of compound of formula (II) the base is selected from the group comprising but not limited to hydroxide or carbonate salt of alkali or alkaline earth metals or organic bases. Preferred base selected form a group comprising lithium hydroxide, potassium hydroxide, sodium hydroxide, calcium hydroxide, sodium carbonate, sodium hydrogen carbonate, potassium carbonate, calcium carbonate, cesium carbonate and the likes. More preferably base is carbonate of sodium or potassium and most preferably sodium carbonate.

In some embodiment, the solvent employed in step (i) of the process for the preparation of compound of formula (II) is selected from the group including but not limited to class of hydrocarbons, halogenated hydrocarbons, esters, ethers, alcohols, water or mixture thereof. Preferably toluene, xylene, hexane, heptane, cyclohexane, dichloromethane, dichloroethane, trichloromethane, ethyl acetate, methyl acetate, propyl acetate, diethyl ether, diisopropyl ether, water or the mixture thereof, most preferably toluene.

In some embodiment, the N-acylation reaction of the step (i) of the process for the preparation of compound of formula (II) is performed under condition sufficient to allow formation of compound (2S)—N-(5-methoxy-1,2,3,4-tetrahydro-naphthalen-2-yl)-N-propyl-2-thiophen-2-yl-acetamide of formula (III) or salt thereof which include but not limited to heating or cooling, stirring the reaction mass for sufficient duration. The formed compound of formula (III) or salt thereof is isolated from the reaction mass by the techniques known in the state of art, preferably involving the steps of separating the immiscible organic solvent and removing the immiscible organic solvent to obtain a residue that is purified by methods known in the state of art.

In some embodiment, demethylation of step (ii) of the process for the preparation of compound of formula (II) is carried out in the presence of from 0.5 to 8, advantageously from 1 to 3, mole of aluminium chloride per mole of starting material.

In some embodiment, the solvent employed in step (ii) may be selected from the group including but not limited to class of hydrocarbons, halogenated hydrocarbons or mixture thereof. Preferably toluene, xylene, hexane, heptane, cyclohexane, dichloromethane, dichloroethane, trichloromethane, monochlorobenzene or the mixtures thereof, most preferably toluene.

The removal of polar organic solvent in step (ii) of the present invention is carried out by techniques and methods including but not limited to distillation or distillation under reduced pressure, evaporation, or the like.

Yet another aspect of the present invention is to provide a process for the preparation of compound (2S)—N-(5-hydroxy-1,2,3,4-tetrahydro-naphthalen-2-yl)-N-propyl-2-thiophen-2-yl-acetamide of formula (II) or its salt thereof,

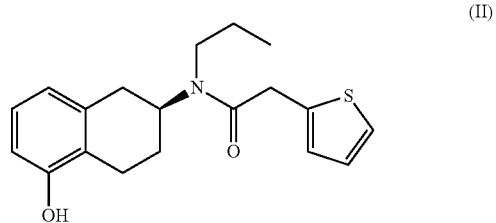 [SMILES: CCCN(C(=O)Cc1cccs1)[C@H]1CCc2c(O)cccc2C1]

by demethylating a compound (2S)—N-(5-methoxy-1,2,3,4-tetrahydro-naphthalen-2-yl)-N-propyl-2-thiophen-2-yl-acetamide of formula (III) or its salt thereof,

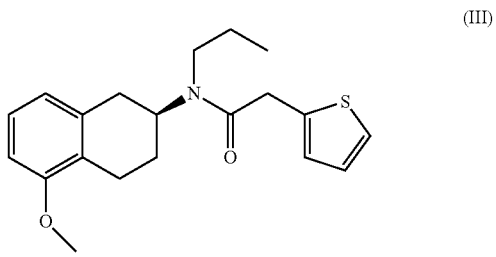 [SMILES: CCCN(C(=O)Cc1cccs1)[C@H]1CCc2c(cccc2OC)C1]

with aluminium chloride to obtain a compound (2S)—N-(5-hydroxy-1,2,3,4-tetrahydro-naphthalen-2-yl)-N-propyl-2-thiophen-2-yl-acetamide of formula (II) or its salt thereof.

In some embodiment of the invention, the demethylation in the above described process for the preparation of compound of formula (II) is carried out in the presence of from 0.5 to 8, advantageously from 1 to 3, mole of aluminium chloride per mole of starting material.

The solvent employed in demethylation step is selected from the group including but not limited to class of hydrocarbons, halogenated hydrocarbons or mixtures thereof. Preferably toluene, xylene, hexane, heptane, cyclohexane, dichloromethane, dichloroethane, trichloromethane, monochlorobenzene or the mixture thereof, most preferably toluene.

The removal of polar organic solvent in demethylation step of the present invention is carried out by techniques and methods including but limited to distillation or distillation under reduced pressure, evaporation or the like.

Rotigotine Form I and Form II are known in the state of art. In some embodiment, the Rotigotine prepared by the invented process is Form I. In some embodiment, the Rotigotine Form I prepared by present process of the invention is stable for more than 3 months at 20-40° C. and 65%-75% of relative humidity.

The present invention is explained in detail with reference to the following examples described below, which are given for the purpose of illustration only and are not intended to limit the scope of the invention.

EXAMPLES

Example 1: Preparation of (2S)—N-(5-methoxy-1,2,3,4-tetrahydro-naphthalen-2-yl)-N-propyl-2-thiophen-2-yl-acetamide of Formula (III)

To a mixture of (S)-1,2,3,4-tetrahydro-5-methoxy-N-propyl-2-naphthalenamine hydrochloride of formula-IV (10 g) and aqueous sodium carbonate (12.4 g of sodium carbonate in 80 ml of water), dichloromethane (80 ml) was added at 27° C. and maintained the reaction mixture for 1 hour. 2-Thiophene acetyl chloride solution (6.9 g of 2-Thiophene acetyl chloride in 80 ml of dichloromethane) was slowly added to the reaction mass at 27° C. and maintained for 1 hour at the same temperature. The progress of the reaction was monitored by TLC. After completion of the reaction, the organic layer of the reaction mixture was separated. The separated organic layer was washed with water (500 ml); and then concentrated under reduced pressure to obtain the titled product as a viscous liquid. % Yield: 94%.

Example 2: Preparation of the Compound of Formula II

To a mixture of viscous liquid obtained in Example 1 (12.7 g) and toluene (100 ml), aluminium chloride (31.3 g) was added at 27° C. Triethylamine (31.7 g) was added to the reaction mixture at 30° C. then heated to 107° C. The heated reaction mixture was maintained for 3 hours and the progress of the reaction was monitored by TLC. After completion of the reaction, the reaction mass was cooled to 5° C. and quenched with IN hydrochloric acid solution (100 ml) to form a biphasic mixture. The organic layer was separated from the biphasic mixture and washed with water (100 ml) followed by 20% sodium chloride solution (100 ml). The resulted organic layer was concentrated under reduced pressure to obtain a residue. The residue was then slurried with methyl tert-butyl ether (60 ml) and then filtered to obtain the titled product. % Yield: 61%.

Example 3: Preparation of Rotigotine Hydrochloride

To a solution of the product obtained in Example 2 (50 g) in toluene (400 ml), borane dimethyl sulphide (23.1 g) was slowly added at 30° C. and the reaction mixture was heated to 60° C. Then the heated reaction mixture was maintained for 10 hours at 55° C. The progress of the reaction was monitored by HPLC. After completion of the reaction, the reaction mass was cooled to 5° C. followed by the addition of 20% aqueous potassium carbonate solution (500 mL) then the reaction mixture was heated to 50° C. and maintained the same temperature for 5 hours. The toluene layer from the reaction mixture was separated and washed with 10% sodium chloride solution (250 ml). Isopropanolic hydrochloride solution (30 ml) was added to the washed toluene layer at 30° C. The resultant reaction mass was concentrated under reduced pressure to obtain a residue. The obtained residue was mixed with ethyl acetate (400 ml) and refluxed for 1 hour at 60° C. The refluxed reaction mass was cooled to 30° C. and maintained at the same temperature for 1 hour. The resultant solid was filtered and washed with ethyl acetate (100 ml) and dried to obtain the titled product. % Yield: 71%.

Example 4: Preparation of Rotigotine Free Base

To an aqueous solution of sodium carbonate (11.94 g of sodium carbonate in 200 ml of water) and the product obtained in Example 3 (25 g), ethyl acetate (200 ml) was added at 30° C. to form a biphasic mixture and stirred 30° C. for 2 hours. The ethyl acetate layer was separated from the biphasic system and the separated ethyl acetate layer was washed with water (200 ml). The obtained ethyl acetate layer was concentrated under reduced pressure to obtain a residue. The obtained residue was mixed with ethyl acetate (10 ml), followed by the addition of hexane (250 ml). The contents were heated to 60° C. and maintained for 1 hour then cooled to 10° C. The cooled contents were stirred for 2 hours at 10° C. The resultant solid was filtered, washed with hexane (50 ml) and dried to obtain Rotigotine free base. % Yield: 61%.

Example 5: Preparation the Compound of Formula (II)

To a solution of aqueous sodium carbonate (186.3 g of sodium carbonate in 1500 ml of water) and (S)-1,2,3,4-tetrahydro-5-methoxy-N-propyl-2-naphthalenamine hydrochloride (150 gm), dichloromethane (1200 ml) was added at 27° C. and maintained the reaction mixture for 1 hour. 2-Thiophene acetyl chloride solution (103.5 g of 2-Thiophene acetyl chloride in 300 ml of dichloromethane) was slowly added to the reaction mass at 27° C. and maintained for 1 hour at the same temperature. The progress of the reaction was monitored by HPLC. After completion of the reaction, the organic layer of the reaction mass was separated. The separated organic layer was washed with water (750 ml) followed by 20% of sodium chloride solution (150 g of sodium chloride in 600 ml of water); and then concentrated under reduced pressure followed by co-concentrated with toluene (1765 ml). Thiourea (134 g) was added to the concentrated mass followed by the addition of aluminium chloride (234.4 gm) under nitrogen atmosphere then heated to 65° C. and maintained the reaction temperature for 6 hours. The progress of the reaction was monitored by HPLC. After completion of the reaction, the reaction mass was cooled to 5° C. and quenched with water (2500 ml) to form a biphasic mixture. The organic layer was separated from the biphasic mixture followed by washing with water (1005 ml). The washed organic layer was concentrated under reduced pressure followed by the addition of n-heptane (974 ml) then heated to 65° C. and maintained the same temperature for 1 hour. Resulting reaction mixture was cooled to 27° C. and maintain the same temperature for 1 hour. The resulted mass was filtered and washed with n-heptane (197 ml). The obtained wet material was recrystallize with toluene (97 ml) and dried to obtain the titled compound. % Yield: 85%.

Example 6: Preparation of Rotigotine

Step-a:
To a solution of the product obtained in Example 5 (100 gm) in toluene (1315 ml) was heated to 55° C. and partially concentrated under reduced pressure followed by the slow addition of borane dimethyl sulphide (379 g) at 30° C. then heated to 90° C. The heated reaction mixture was maintained for 5 hours at 90° C. The progress of the reaction was monitored by HPLC. After completion of the reaction, the reaction mass was cooled to 25° C. followed by the addition of freshly prepared aqueous dimethylamine solution (158.3 g of 40% dimethyl amine with 172 ml of water) to form a biphasic mixture and heated to 40° C. The heated biphasic mixture was maintained for 12 hours at 40° C. The organic layer was separated, washed with water (1000 ml) and concentrated under reduced pressure followed by cooling at 25° C. The diluted hydrochloric acid (37 g of concentrated HCl with 200 ml of water) was added to the cooled mass at 25° C. and maintained the same temperature for 3 hours. The resulted mass was filtered and washed with water (300 ml) to provide wet product.

Step-b:
To a mixture of the product obtained from step-a and dichloromethane (527 ml), methanol (162 ml) was added at 45° C. followed by the addition of water (100 ml). Then the reaction mixture was maintained at the same temperature for 1 hour followed by cooling at 5° C. and maintained the same temperature for 3 hours. The obtained mass was filtered, washed with dichloromethane (200 ml) and water (500 ml) to obtain a wet product.

Step-c:

To a mixture of the product obtained in step-b and ethylacetate, aqueous sodium bicarbonate solution (48 g of sodium bicarbonate dissolved in 800 ml of water) was added at 30° C. to form a biphasic mixture and maintained for 2 hours. The organic layer was separated from the reaction mixture and treated with activated carbon at 30° C. then filtered through hyflo bed. The resulted filtrate was concentrated under reduced pressure then co-concentrated with n-heptane (102 ml) to obtain a residue. N-heptane (731 ml) was added to the resulted residue and maintained for 1 hour at 60° C. The obtained mass was cooled to 30° C.; maintained for 6 hours at 30° C. then filtered, washed with n-heptane (102 ml) and dried to obtain Rotigotine. % Yield: 67%.

We claim:

1. A process for the preparation of compound (2S)—N-(5-hydroxy-1,2,3,4-tetrahydro-naphthalen-2-yl)-N-propyl-2-thiophen-2-yl-acetamide of formula (II) or its salt thereof, an intermediate useful in the preparation of Rotigotine,

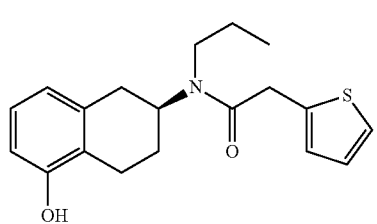
(II)

comprising the steps of:
(i) reacting the compound (S)-1,2,3,4-tetrahydro-5-methoxy-N-propyl-2-naphthalenamine of formula (IV) or its salt thereof

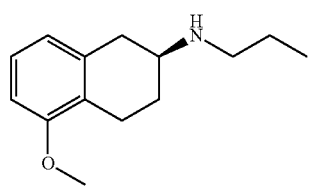
(IV)

with 2-thienylacetic acid derivative of formula (V) or its salt thereof

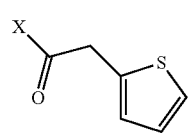
(V)

wherein X represent leaving group in presence of a base to obtain a compound (2S)—N-(5-methoxy-1,2,3,4-tetrahydro-naphthalen-2-yl)-N-propyl-2-thiophen-2-yl-acetamide of formula (III) or its salt thereof; and

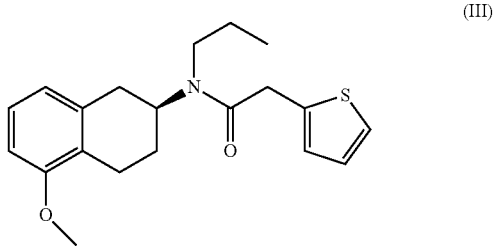 [SMILES: CCCN(C(=O)Cc1cccs1)[C@H]1CCc2c(cccc2OC)C1]
(III)

(ii) demethylating the compound (2S)—N-(5-methoxy-1,2,3,4-tetrahydro-naphthalen-2-yl)-N-propyl-2-thiophen-2-yl-acetamide of formula (III) or its salt thereof as obtained in step (i) with aluminium chloride to obtain a compound (2S)—N-(5-hydroxy-1,2,3,4-tetrahydro-naphthalen-2-yl)-N-propyl-2-thiophen-2-yl-acetamide of formula (II) or its salt thereof.

2. The process as claimed in claim 1, wherein said base is selected from the group comprising hydroxide or carbonate salt of alkali or alkaline earth metals.

3. The process as claimed in claim 1, wherein said base is selected from the group comprising organic bases.

4. The process as claimed in claim 2, wherein said base is selected from the group comprising lithium hydroxide, potassium hydroxide, sodium hydroxide, calcium hydroxide, sodium carbonate, sodium hydrogen carbonate, potassium carbonate, calcium carbonate or cesium carbonate.

5. A process for the preparation of compound (2S)—N-(5-hydroxy-1,2,3,4-tetrahydro-naphthalen-2-yl)-N-propyl-2-thiophen-2-yl-acetamide of formula (II) or its salt thereof,

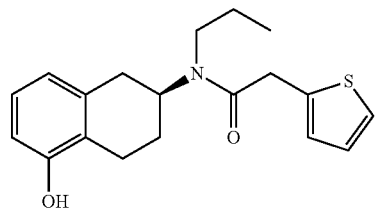
(II)

by demethylating a compound (2S)—N-(5-methoxy-1,2,3,4-tetrahydro-naphthalen-2-yl)-N-propyl-2-thiophen-2-yl-acetamide of formula (III) or its salt thereof,

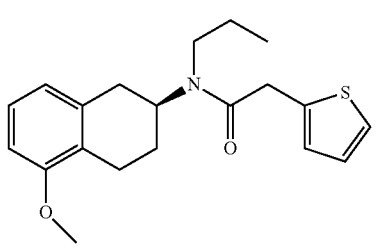
(III)

with aluminium chloride to obtain a compound (2S)—N-(5-hydroxy-1,2,3,4-tetrahydro-naphthalen-2-yl)-N-propyl-2-thiophen-2-yl-acetamide of formula (II) or its salt thereof.

6. The process as claimed in claim 1, wherein the obtained compound (2S)—N-(5-hydroxy-1,2,3,4-tetrahydro-naphthalen-2-yl)-N-propyl-2-thiophen-2-yl-acetamide of formula (II) or its salt thereof is further converted to Rotigotine of formula (I) or its salts thereof in presence of a suitable reducing agent and a solvent

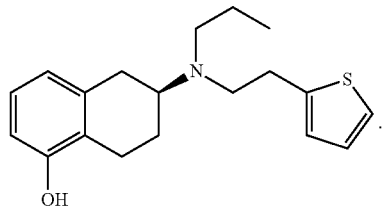

(I)

* * * * *